(12) United States Patent
Matin et al.

(10) Patent No.: US 9,999,581 B2
(45) Date of Patent: Jun. 19, 2018

(54) LIQUID MOUTHWASH

(71) Applicant: Hychlotech Medical Japan Co., Ltd, Chiyoda-ku, Tokyo (JP)

(72) Inventors: Khairul Matin, Tokyo (JP); Junji Tagami, Tokyo (JP); Kenichi Nebuka, Tokyo (JP); Tamon Fujiwara, Tokyo (JP); Akihiko Katayama, Hokkaido (JP)

(73) Assignee: HYCHLOTECH MEDICAL JAPAN CO., LTD., Tokyo (JP)

( * ) Notice: Subject to any disclaimer, the term of this patent is extended or adjusted under 35 U.S.C. 154(b) by 0 days. days.

(21) Appl. No.: 14/910,495

(22) PCT Filed: Aug. 6, 2014

(86) PCT No.: PCT/JP2014/070793
§ 371 (c)(1),
(2) Date: Feb. 5, 2016

(87) PCT Pub. No.: WO2015/020116
PCT Pub. Date: Feb. 12, 2015

(65) Prior Publication Data
US 2016/0175208 A1    Jun. 23, 2016

(30) Foreign Application Priority Data

Aug. 7, 2013   (JP) .................................. 2013-164611

(51) Int. Cl.
| | |
|---|---|
| *A61K 8/34* | (2006.01) |
| *A61K 8/19* | (2006.01) |
| *A61K 8/46* | (2006.01) |
| *A61Q 11/00* | (2006.01) |

(52) U.S. Cl.
CPC .................. *A61K 8/34* (2013.01); *A61K 8/19* (2013.01); *A61K 8/345* (2013.01); *A61K 8/46* (2013.01); *A61K 8/463* (2013.01); *A61K 8/466* (2013.01); *A61Q 11/00* (2013.01); *A61K 2800/49* (2013.01); *A61K 2800/591* (2013.01); *A61K 2800/882* (2013.01)

(58) Field of Classification Search
USPC .................... 424/49, 78.04; 422/37
See application file for complete search history.

(56) References Cited

U.S. PATENT DOCUMENTS

| | | | | |
|---|---|---|---|---|
| 5,723,106 | A  * | 3/1998 | Buch ........................ | A61K 8/34 |
| | | | | 424/49 |
| 6,426,066 | B1 * | 7/2002 | Najafi .................... | A61K 33/14 |
| | | | | 424/613 |
| 2006/0253060 | A1 * | 11/2006 | Alimi ................... | A61C 1/0076 |
| | | | | 604/19 |
| 2013/0078196 | A1 | 3/2013 | Noguchi | |

FOREIGN PATENT DOCUMENTS

| | | |
|---|---|---|
| CN | 101189017 A | 5/2008 |
| JP | 05007876 A | 1/1993 |
| JP | 06145033 A | 5/1994 |
| JP | 09183706 A | 7/1997 |
| JP | 10087462 A | 4/1998 |
| JP | 2006068354 A | 3/2006 |
| JP | 2008260740 A | 10/2008 |
| KR | 1020080011312 A | 2/2008 |
| WO | 2006119300 A2 | 11/2006 |
| WO | 2007072697 A1 | 6/2007 |
| WO | 2009098870 A1 | 8/2009 |

OTHER PUBLICATIONS

Storehagen et al., "Dentifrices and Mouthwashes Ingredients and Their Use." Institute for Clinical Odontology, 2003; Sem 10, V99; pp. 1-49.*
International Search Report corresponding to Application No. PCT/JP2014/070793; dated Dec. 9, 2014, with English translation.
KIPO Office Action corresponding to KR Application No. 10-2016-7005924; dated May 4, 2017.
SIPO Office Action corresponding to Application No. 201480046813.2; dated Feb. 13, 2018.

* cited by examiner

*Primary Examiner* — Walter E Webb
(74) *Attorney, Agent, or Firm* — Cantor Colburn LLP

(57) ABSTRACT

Provided is a liquid mouthwash that is capable of maintaining a bactericidal effect over a long period, and uses electrolyzed water that inhibits metal corrosion. The liquid mouthwash contains electrolyzed water having a positive oxidation-reduction potential, a menthol, an anionic surfactant, and a water-soluble organic solvent, and has a pH of 6 to 8. The electrolyzed water, and the menthol or one or more anionic surfactants are accommodated without coming into contact with each other, and are preferably used in a mixed state at the time of use.

3 Claims, 11 Drawing Sheets

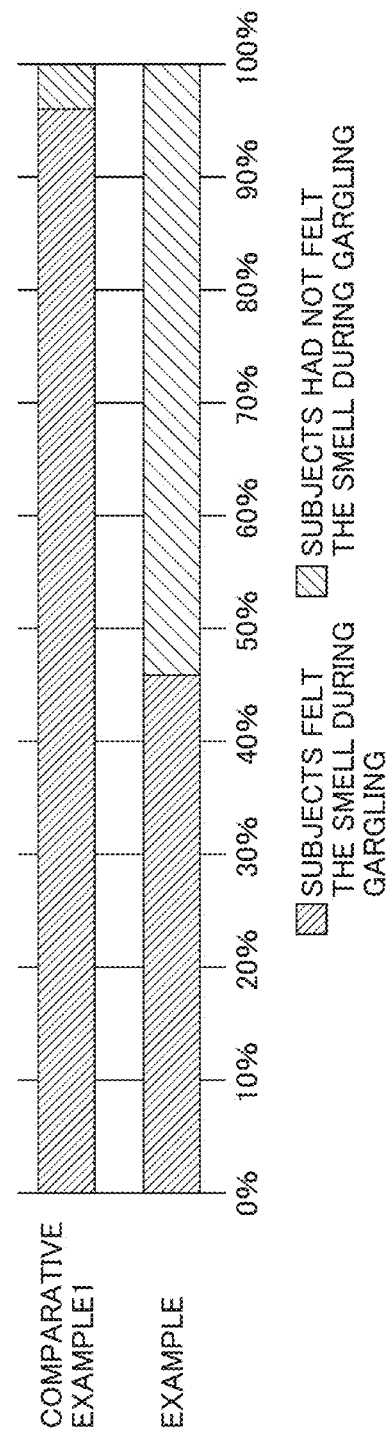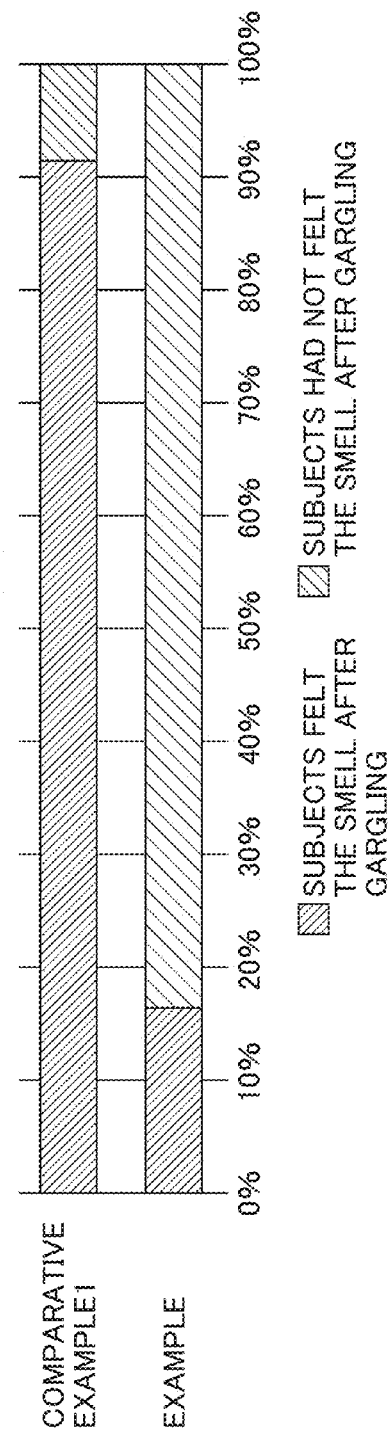

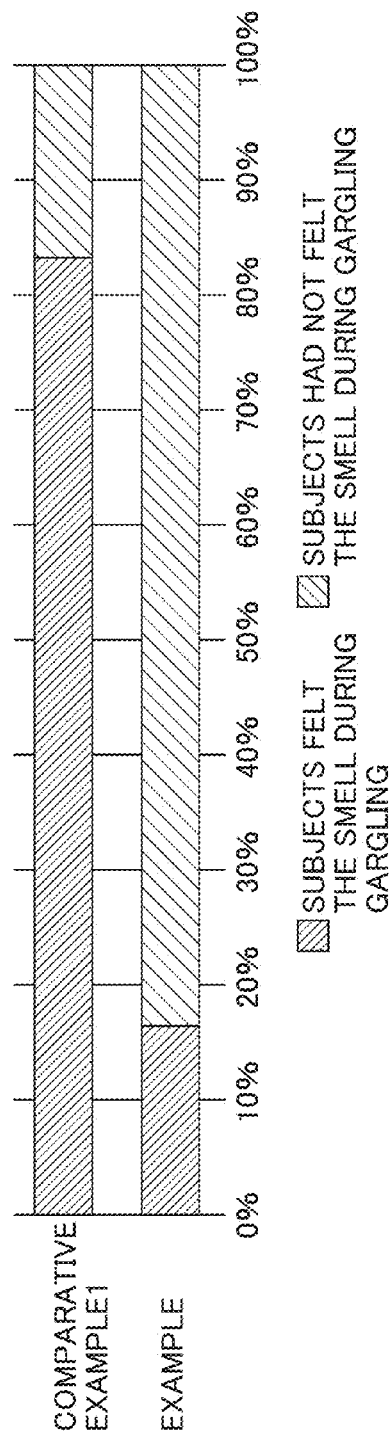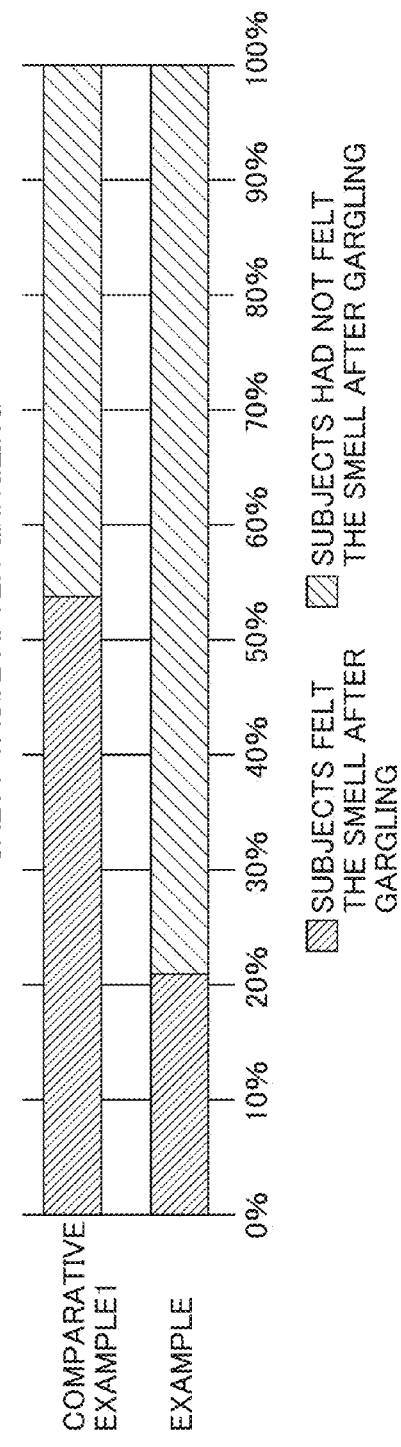

LIQUID MOUTHWASH

CROSS REFERENCE TO RELATED APPLICATIONS

This is the U.S. national stage of application No. PCT/JP2014/070793, filed on Aug. 6, 2014. Priority under 35 U.S.C. § 119(a) and 35 U.S.C. § 365(b) is claimed from Japanese Application No. 2013-164611, filed Aug. 7, 2013, the disclosure of which is also incorporated herein by reference.

TECHNICAL FIELD

The present invention relates to a liquid mouthwash.

BACKGROUND ART

Caries, which is a typical example of oral bacterial diseases, is one of two major dental diseases together with a periodontal disease and is a loss of tooth structure caused by erosion (demineralization) of the minerals forming enamel or dentin with acids, such as lactic acid, generated by caries-causing bacteria proliferated on the surface of tooth structure.

In the process of developing caries, a biofilm is formed on the surface of tooth structure. The formation of the biofilm on the surface of tooth structure demineralizes the tooth structure just below the biofilm, leading to caries.

Accordingly, in order to prevent caries, for example, caries-causing bacteria are prevented from proliferating or are sterilized; the biofilm is removed with mechanical means; or the demineralized tooth structure is remineralized.

Among these methods, the proliferation inhibition or sterilization of caries-causing bacteria does not need any special device in its application and is broadly applied. A typical example thereof is gargling with an oral rinse containing a caries-causing bacterium proliferation-inhibiting or sterilizing component. These methods inhibit proliferation of caries-causing bacteria on the surface of tooth structure to prevent the tooth structure from being demineralized, leading to effective prevention of caries.

In particular, a hypochlorous acid solution, which can be prepared by electrolysis of an aqueous solution of a chloride such as sodium chloride, has a high bactericidal effect and is thereby proposed to be used as a liquid mouthwash for dental treatment (Patent Literatures 1 to 4).

Patent Document 1: Japanese Unexamined Patent Application, Publication No. H09-183706
Patent Document 2: Japanese Unexamined Patent Application, Publication No. H10-087462
Patent Document 3: PCT International Publication No. WO2007/072697
Patent Document 4: PCT International Publication No. WO2009/098870

DISCLOSURE OF THE INVENTION

Problems to be Solved by the Invention

However, the liquid mouthwash containing electrolyzed water has insufficient stability and difficulty in maintaining the bactericidal effect for a long time after production and has problems in the flavor, for example, giving a distinctive chlorine smell or a strong salty taste when being kept in the mouth. Since the presence of a flavoring agent or other agents that are usually used for improving the flavor of a liquid mouthwash particularly accelerate the decomposition of electrolyzed water, such agents cannot be used. In addition, electrolyzed water has an effect of eroding metals and thereby causes the problem of highly affecting devices that are used for, for example, intraoral treatment.

The present invention has been made under the above-described circumstances, and an object thereof is to provide a liquid mouthwash containing electrolyzed water that can maintain the bactericidal effect for a long time and have reduced metal corrosive properties.

Means for Solving the Problems

The present inventors have found that a liquid mouthwash containing a specific additive, in addition to electrolyzed water having a positive oxidation-reduction potential, it can prevent the electrolyzed water from deteriorating to maintain the bactericidal effect for a long time and can reduce the metal corrosive properties, and have accomplished the present invention. More specifically, the present invention provides the followings.

The present invention provides a liquid mouthwash containing electrolyzed water having a positive oxidation-reduction potential, a menthol, an anionic surfactant, and a water-soluble organic solvent and having a pH of 6 to 8.

Effects of the Invention

The present invention can provide a liquid mouthwash containing electrolyzed water that can maintain the bactericidal effect for a long time and has reduced metal corrosive properties.

BRIEF DESCRIPTION OF THE DRAWINGS

FIG. 1A includes diagrams showing the questionnaire results on chlorine smell of the liquid mouthwash of the present invention.

FIG. 1B includes diagrams showing the questionnaire results on chlorine smell of the liquid mouthwash of the present invention.

FIG. 2A includes diagrams showing the questionnaire results on salty taste of the liquid mouthwash of the present invention.

FIG. 2B includes diagrams showing the questionnaire results on salty taste of the liquid mouthwash of the present invention.

PREFERRED MODE FOR CARRYING OUT THE INVENTION

Figure 3:
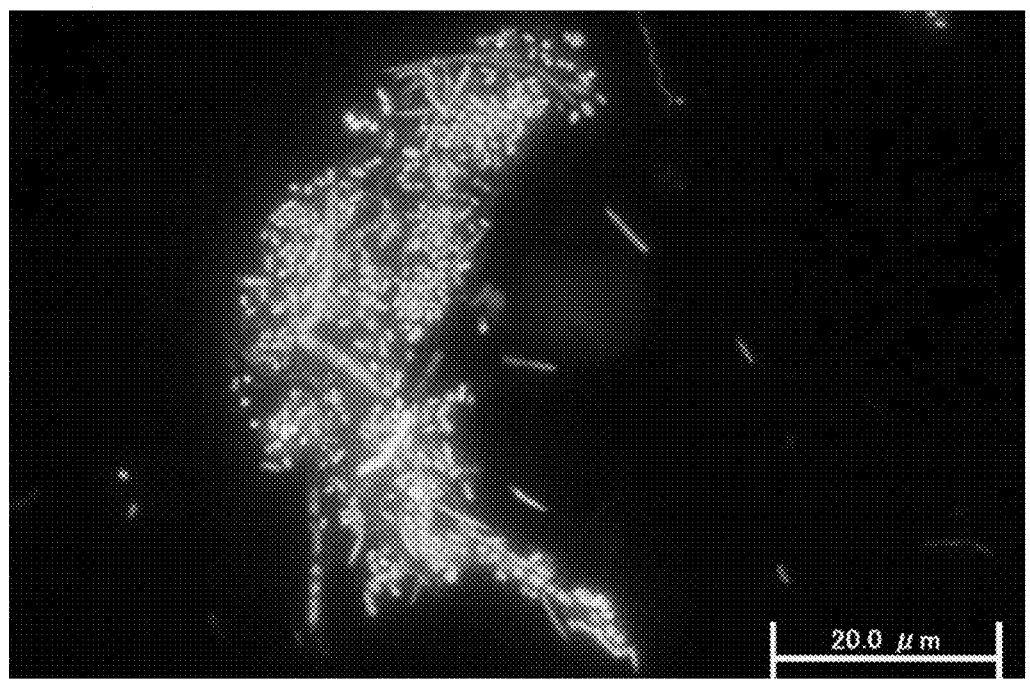
FIG. 3 is a photograph showing the bactericidal activity on oral bacteria (including caries-causing bacteria and periodontal disease bacteria) before the application of the liquid mouthwash of the present invention.

Embodiments of the present invention will now be described in detail, but the invention is not limited to the following embodiments and can be implemented with appropriate modifications within the purpose of the present invention.

The liquid mouthwash of the present invention contains electrolyzed water having a positive oxidation-reduction potential, a menthol, an anionic surfactant, and a water-soluble organic solvent. Raw materials used in the liquid mouthwash of the present invention will now be described.

<Electrolyzed Water Having a Positive Oxidation-Reduction Potential>

Electrolyzed water prepared by adding a chlorine-based electrolyte, such as sodium chloride or potassium chloride, to water and performing electrolysis is known. In particular, two types of electrolyzed water having different properties can be produced by dividing an electrolytic tank into two or more chambers with, for example, ion-exchange membranes and conducting electricity with a pair of electrodes. Herein, the electrolyzed water obtained from the cathode electrode side is called reduced water and is known to have alkalinity and have an effect of decomposing and cleansing organic materials such as oils and fats and proteins. On the other hand, the electrolyzed water obtained from the anode electrode side is called oxidized water and has acidity by containing, for example, hypochlorite ions or chlorine ions and is used for rinsing hands or endoscopes to prevent infectious diseases by its bactericidal effect.

The liquid mouthwash of the present invention contains the latter, i.e., the electrolyzed water having a positive oxidation-reduction potential obtained from the anode side. More specifically, the present invention uses electrolyzed water having a positive oxidation-reduction potential obtained from the anode side in electrolysis. The oxidation-reduction potential (ORP) may be any positive potential and is preferably 700 mV or more and more preferably 800 mV or more. The ORP is most preferably 900 mV or more. A positive ORP has a bactericidal activity and is therefore preferred.

The electrolyzed water of the present invention is prepared by electrolysis of water a containing chlorine-based electrolyte and therefore contains chlorine ions. The liquid mouthwash of the present invention has a high bactericidal activity, compared with known liquid mouthwashes containing electrolyzed water. In addition, since chlorine ions contained therein are hardly decomposed and have excellent preservability, the upper limit of the concentration of chlorine ions in the electrolyzed water to be used can be set to be low. The concentration of chlorine ions, however, should be 5 to 250 ppm and is preferably 50 to 200 ppm and more preferably 80 to 150 ppm. A concentration of chlorine ions of 5 ppm or more is preferred for securing the bactericidal activity, and a concentration of 250 ppm or less can suppress the chlorine smell when kept in the mouth and can inhibit metal corrosion.

The electrolyzed water of the present invention can be produced with any known electrolyzer having an electrolytic tank divided into two or more chambers.

A two-chamber electrolyzer has an electrolytic tank divided into two chambers with a single diaphragm (ion-exchange membrane) and electrolyzes water with an anode and a cathode put in the respective chambers. In the use of a two-chamber electrolyzer, a chlorine-based electrolyte, such as sodium chloride or potassium chloride, is added to water in both chambers. The liquid mouthwash of the present invention contains the electrolyzed water generated in the chamber accommodating the anode.

The electrolyzed water of the present invention is more preferably produced with a three-chamber electrolyzer provided with an intermediate chamber between the cathode chamber and the anode chamber. In the three-chamber electrolyzer, usually, the intermediate chamber accommodates a solution, called supporting electrolyte, composed of water and, for example, sodium chloride or potassium chloride; and the cathode chamber and the anode chamber accommodate water. The intermediate chamber is separated from the cathode chamber or the anode chamber with an ion-exchange membrane and the electrode. Conduction of electricity to the cathode and the anode electrolyzes the supporting electrolyte in the intermediate chamber and allows the chlorine ions from the intermediate chamber to pass through the ion-exchange membrane and to dissolve in the water in the anode chamber. The thus-prepared electrolyzed water in the anode chamber has a positive oxidation-reduction potential (ORP) and contains chlorine ions, but does not contain a substantial number of other ions such as sodium ions. Furthermore, after generation of electrolyzed water, the pH of the water can be adjusted to near neutral to prevent the generation of chlorine gas. In contrast, in the use of a two-chamber electrolyzer, the electrolyzed water obtained from the anode side contains a large number of ions, such as sodium ions and potassium ions, in addition to chlorine ions and has a strong acidic pH of 2.2 to 2.7, leading to instability of, for example, hypochlorite ions and chlorine ions contained in the water. As a result, chlorine gas is apt to be generated.

<Menthol>

The liquid mouthwash of the present invention indispensably contains a menthol from the viewpoint of improving the cool sensation in intraoral application and of reducing the metal corrosive properties possessed by the electrolyzed water. Usable examples of the menthol include 1-menthol, d-menthol, and dl-menthol. In particular, 1-menthol is preferred.

The content of the menthol in the composition for mouth of the present invention is preferably 20 mg (0.13 mmol)/L to 100 mg (0.64 mmol)/L, more preferably 30 mg (0.19 mmol)/L to 90 mg (0.58 mmol)/L, and further preferably 40 mg (0.26 mmol)/L to 80 mg (0.51 mmol)/L. A content of 20 mg (0.13 mmol)/L or more is preferred from the viewpoint of improving the cool sensation in application of the mouthwash to oral cavity and the aftertaste by prevention of allotriogeusia through a combination of a surfactant and an oil component and of preventing the metal corrosion. A content of 100 mg (0.64 mmol)/L or less is preferred from the viewpoint of storage stability of the liquid mouthwash.

<Anionic Surfactant>

The present inventors have found through investigation that an anionic surfactant prevents the promotion of decomposition of electrolyzed water accompanied by the addition of a menthol and the metal corrosion of the electrolyzed water, in addition to regular functions of rinsing and sterilization of oral cavity.

The anionic surfactant contained in the liquid mouthwash of the present invention may be any known anionic surfactant that can be used in liquid mouthwashes. Examples of the anionic surfactant include alkylbenzene sulfonates, such as sodium dodecylbenzene sulfonate; α-olefin sulfonates; alkyl sulfate ester salts, such as sodium laurylsulfate and sodium myristylsulfate; N-acyl sarcosinates, such as sodium N-lauroyl sarcosinate and sodium N-myristoyl sarcosinate; sodium hydrogenated coconut fatty acid monoglyceride monosulfate; sodium lauryl sulfoacetate; N-acyl glutamates, such as sodium N-palmitoyl glutamate; N-methyl-N-acyltaurine salts; and N-methyl-N-acylalanine salts. These surfactants may be used in a combination of two or more thereof. Among these surfactants, alkylbenzene sulfonates, α-olefin sulfonates, and alkyl sulfate ester salts are particularly preferred.

The content of the anionic surfactant in the liquid composition for mouth is 5 mg (0.017 mmol)/L to 60 mg (0.21 mmol)/L, preferably 10 mg (0.035 mmol)/L to 50 mg (0.17 mmol)/L, and particularly preferably 20 mg (0.07 mmol)/L to 40 mg (0.139 mmol)/L. A content of 5 mg (0.017 mmol)/L or more provides a sufficient effect as a liquid mouthwash and can prevent the decomposition of electrolyzed water accompanied by the addition of a menthol and can prevent metal corrosion. A content of 60 mg (0.21 mmol)/L or less does not impair the mouthwash preference.

In addition, the anionic surfactant can be used in a combination with a nonionic surfactant. Examples of the nonionic surfactant include polyoxyethylene alkyl ethers, polyoxyethylene alkylallyl ethers, polyoxyethylene/polyoxypropylene alkyl ethers, polyoxyethylene/polyoxypropylene block copolymers, sucrose fatty acid esters, glycerin fatty acid esters, propylene glycol fatty acid esters, sorbitan fatty acid esters, polyoxyethylene sorbitan fatty acid esters, polyoxyethylene sorbitol tetraoleate, alkyl glycoside fatty acid esters, polyoxyethylene sucrose fatty acid esters, polyoxyethylene glycol fatty acid esters, alkyl glycosides, fatty acid monoethanolamide, polyoxyethylene fatty acid monoethanolamide, polyoxyethylene fatty acid diethanolamide, polyoxyethylene castor oil, polyoxyethylene hydrogenated castor oil, and polyoxyethylene beeswax derivatives. These surfactants may be used alone or in a combination of two or more thereof.

The content of the nonionic surfactant is 20 to 60 mg/L, preferably 30 to 50 mg/L, and particularly preferably 35 to 45 mg/L.

<Water-Soluble Organic Solvent>

The liquid mouthwash of the present invention contains a water-soluble organic solvent for dissolving a water-insoluble menthol. The water-soluble organic solvent contained in the liquid mouthwash of the present invention can be any known one that can be used in liquid mouthwashes. Examples thereof include lower alcohols, such as ethanol and propanol; polyhydric alcohols, such as glycerin, ethylene glycol, propylene glycol, and 1,3-butylene glycol; and polyalkylene glycols, such as polyethylene glycol and polypropylene glycol. These solvents may be used alone or in a combination of two or more thereof. Furthermore, use of a less stimulative solvent selected from these solvents is particularly preferred, and a polyhydric alcohol, in particular, glycerin, ethylene glycol, or propylene glycol, is preferably used.

The content of the water-soluble organic solvent in the liquid mouthwash is 2.5 to 8 mol/L, preferably 4 to 6.6 mol/L, and particularly preferably 4.6 to 5.9 mol/L. A content of at least 2.5 mol/L can prevent precipitation of the menthol. A content of 8 mol/L or less does not cause stimulation in the use and does not impair the safety of the liquid mouthwash and is preferred.

<Alkaline Agent>

The liquid mouthwash of the present invention may contain an alkaline agent for adjusting the pH to an appropriate range. Any known alkaline agent that does not adversely affect humans can be used.

The liquid mouthwash of the present invention preferably has a pH of 6 to 8, more preferably 6.5 to 7.5. A pH in this range does not stimulate or damage oral tissues and stabilizes chlorine ions and the like contained in the mouthwash to enhance the preservability, and is therefore preferred.

Usable examples of the alkaline agent include alkali metal salts or ammonium salts of organic acids such as citric acid, fumaric acid, and malic acid; alkali metal salts or ammonium salts of inorganic acids such as phosphoric acid and carbonic acid; and hydroxides of alkali metals. Preferred are inorganic alkaline agents, such as sodium hydroxide, potassium hydroxide, sodium carbonate, and potassium carbonate, and particularly preferred is sodium hydroxide.

The addition amount of the alkaline agent varies depending on the type of the used alkaline agent, the pH of the electrolyzed water, and the type and the content of the anionic surfactant is preferably an amount necessary for adjusting the pH as the total of the liquid mouthwash in the above-mentioned range. The amount is preferably 7 to 9 mmol/L, more preferably 7.8 to 8.8 mmol/L, and further preferably 8.2 to 8.5 mmol/L. An addition amount within this range does not stimulate or damage oral tissues and stabilizes chlorine ions and the like contained in the mouthwash to enhance the preservability, and is therefore preferred.

The liquid mouthwash of the present invention can contain, in addition to the above-mentioned components, for example, a moistening agent, a preservative, a fluoride, an efficacious agent, an enzyme, a pigment, a flavoring agent other than menthol, a sweetener, and a thickener that are usually used as components of liquid mouthwashes, within a range that does not impair the purpose of the present invention.

<Liquid Mouthwash>

The liquid mouthwash of the present invention may be a one-component type mouthwash in which electrolyzed water having a positive oxidation-reduction potential contains a menthol, an anionic surfactant, a water-soluble organic solvent, and an alkaline agent or may be a two-component type mouthwash in which electrolyzed water and at least one of a menthol and an anionic surfactant are separately accommodated not to be in contact with each other. In a two- or more component type liquid mouthwash, the components are mixed immediately before the use to prepare an appropriate amount of the final liquid mouthwash, or the components are mixed to prepare a certain amount of the final liquid mouthwash, and an appropriate amount thereof is used at each time.

Although the liquid mouthwash of the present invention has sufficient preservability even in a one-component type form, a two-component type can maintain the bactericidal effect for a longer time and is therefore preferred. It is particularly important that the electrolyzed water and at least one of the menthol and the anionic surfactant are not in contact with each other, from the point of preventing decomposition of the electrolyzed water and maintaining the effect.

Considering the incompatibility between preservability and handling for mixing, a two-component type liquid mouthwash is more preferred.

The liquid mouthwash of the present invention can be produced by any known method with any known device. A one-component type liquid mouthwash can be produced by, for example, adding a menthol to a water-soluble organic solvent to dissolve the menthol at 10° C. to 65° C., preferably 20° C. to 55° C., adding the resulting uniform solution to electrolyzed water having a positive oxidation-reduction potential, and then adding an anionic surfactant and an alkaline agent thereto. In a two-component type, for example, a menthol and an alkaline agent are added to a water-soluble organic solvent and are uniformly dissolved as in above to give a first solution. Subsequently, electrolyzed water having a positive oxidation-reduction potential is mixed with an appropriate amount of an alkaline agent to give a second solution. In both the one-component type and the two-component type, when the liquid mouthwash contains an oil-soluble component as an additional component, it is preferable to dissolve the oil-soluble component in a water-soluble organic solvent first.

An appropriate amount in each use of the liquid mouthwash of the present invention is about 20 mL. The mouthwash is used by keeping it in the mouth for from several ten seconds to several minutes and then spitting it. For example, in order to prevent various dental diseases, the mouthwash is preferably used in each home after each tooth-brushing. However, the use of twice a day, morning and evening, also has a sufficient effect. In addition, the mouthwash is preferably used for treatment in a dental clinic as sterilized water for treatment of dental diseases. More specifically, the mouthwash is effective for treatment of, for example, decayed teeth, periodontal diseases, and halitosis.

EXAMPLES

Subsequently, the present invention will be described in further detail based on Example, but is not limited thereto.

[Production of Liquid Mouthwash]

Example

A three-chamber electrolyzer (manufactured by Redox Inc.) was used to prepare electrolyzed water having a residual chlorine concentration of 125 ppm and an ORP of 905 mV from the anode tank, followed by further addition of 8 mol/L of sodium hydroxide to adjust the pH to about 7. 80 mg/L of 1-menthol, 80 mL/L of propylene glycol (PG), and 40 mg/L of sodium dodecylsulfate (SDS) were dissolved in this electrolyzed water to give a liquid mouthwash having a pH of about 7.

Comparative Example 1

A commercially available liquid mouthwash containing electrolyzed water was directly used.

Comparative Example 2

Only the electrolyzed water used in Example was used as a comparative liquid mouthwash.

Comparative Example 3

A liquid mouthwash prepared as in Example except that sodium dodecylsulfate (SDS) was not added was used as a comparative liquid mouthwash.

Comparative Example 4

A liquid mouthwash prepared as in Example except that 1-menthol and propylene glycol (PG) were not added was used as a comparative liquid mouthwash.

[Evaluation of Chlorine Smell and Salty Taste]

Chlorine smell and salty taste of the liquid mouthwashes of Example and Comparative Example 1 when kept in the mouth were evaluated by means of questionnaires to 24 subjects after they had gargled with the liquid mouthwashes. The results are shown in FIGS. 1 and 2.

The results shown in FIGS. 1A and 1B demonstrated that the number of subjects felt chlorine smell in the liquid mouthwash of the present invention was smaller than that in the commercially available liquid mouthwash containing electrolyzed water in both during gargling (FIG. 1A) and after gargling (FIG. 1B) and confirmed that the liquid mouthwash of the present invention can be used without any particular problem. Similarly, the results shown in FIGS. 2A and 2B demonstrated that the number of subjects felt salty taste in the liquid mouthwash of the present invention was smaller than that in the commercially available liquid mouthwash containing electrolyzed water in both during gargling (FIG. 2A) and after gargling (FIG. 2B) and revealed that the liquid mouthwash of the present invention is remarkably easy to use.

[Evaluation of Preservability]

The chlorine concentration of each of the liquid mouthwashes of Example and Comparative Examples was measured. Subsequently, each of the liquid mouthwashes was placed in a container and was stored at room temperature for one month. The reduction in the chlorine concentration after the storage for one month was measured.

[Evaluation of Metal Corrosive Properties]

Each of the liquid mouthwashes of Example and Comparative Examples were added to a plastic container accommodating one stainless steel iron nail and was left to stand at room temperature for 15 min. The change in the solution was observed. The mouthwash changed in color to brown was rated as poor, the mouthwash slightly colored was rated as moderate, and the mouthwash exhibited no change was rated as excellent.

Table 1 shows the evaluation results of the preservability and metal corrosive properties of the mouthwashes of Example and Comparative Examples.

TABLE 1

| | Specifications | Rate of disappearance of chlorine after one month | Metal corrosive properties |
|---|---|---|---|
| Comparative Example 1 | Commercially available liquid mouthwash containing electrolyzed water | 30.9-40% | poor |
| Comparative Example 2 | Electrolyzed water only | 15% | poor |
| Comparative Example 3 | Electrolyzed water, menthol liquid, and PG | 50-99% | moderate |
| Comparative Example 4 | Electrolyzed water and SDS | — | poor |
| Example | Electrolyzed water, 1-menthol, PG, and SDS | 15% | excellent |

It was demonstrated that the liquid mouthwash consisting of electrolyzed water only of Comparative Example 2 had a small rate of disappearance of chlorine after one month and had hardly decomposed with time, but had high metal corrosive properties. In contrast, in the electrolyzed water containing 1-menthol and PG of Comparative Example 3, the decomposition rate was accelerated. Meanwhile, the liquid mouthwash containing all of 1-menthol, PG, and SDS of Example was prevented from being decomposed, which was equal to that consisting of electrolyzed water only of Comparative Example 2. The liquid mouthwash was demonstrated not to have metal corrosive properties and also to be excellent in the points of the rate of disappearance of chlorine and metal corrosive properties compared with those of commercial products.

[Evaluation of Bactericidal Effect 1]

Gargling with the liquid mouthwash of Example was performed, and the bactericidal effect on oral bacteria was verified. FIG. 3 shows the oral bacteria collected from a periodontal pocket before gargling with the liquid mouthwash of Example. It was revealed that the shapes of almost all of the cells were clearly viewable. These clearly viewable portions indicate live bacteria (living bacteria).

Figure 4:
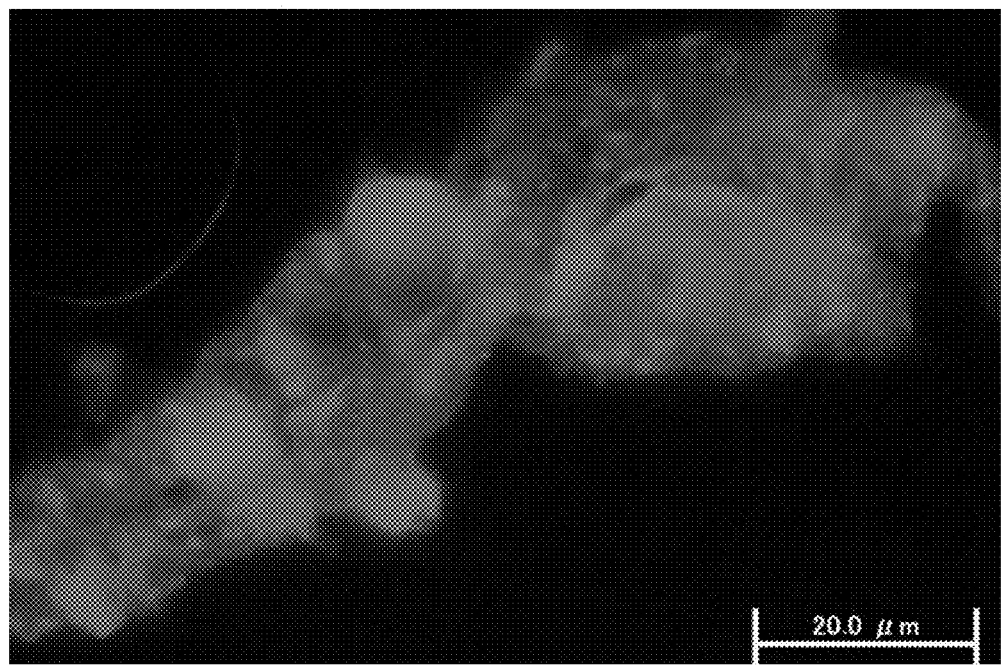
FIG. 4 is a photograph showing oral bacteria after application of the liquid mouthwash of the present invention.

In contrast, FIG. 4 shows the appearance of oral bacteria collected from a periodontal pocket after gargling with the liquid mouthwash of Example. The colorless portion appearing dark indicates killed bacteria. It was observed that almost all of bacteria were dead. This confirmed that the liquid mouthwash of the present invention effectively showed the bactericidal effect in oral cavity. Furthermore, it was confirmed by the same investigation on the bacteria in a biofilm formed on the surface of teeth that the liquid mouthwash of the present invention was similarly effective on the bacteria in a biofilm.

Figure 5:
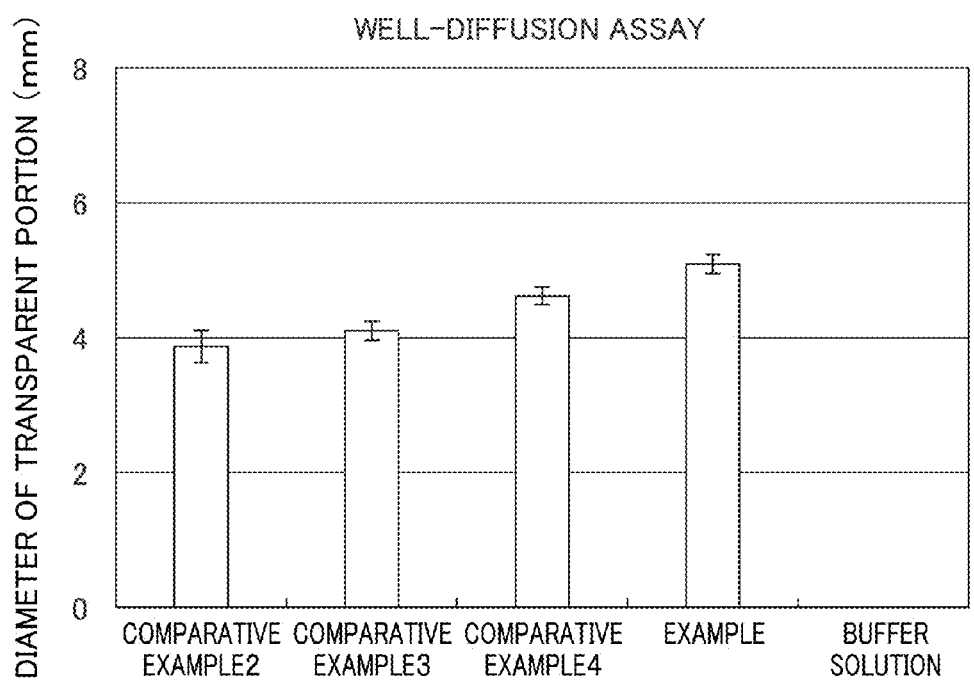
FIG. 5 is a graph showing the bactericidal activity of the liquid mouthwash of the present invention on caries-causing bacteria, compared with respect to each raw material.

Subsequently, the effect of the liquid mouthwash of the present invention on caries-causing bacteria (*S. mutans*) was validated by well-diffusion assay. Caries-causing bacteria were added to an agar culture medium and were then dispensed into a petri dish. The solidified culture medium was perforated with holes having a diameter of about 4 mm, and 10 μL of each of the liquid mouthwashes of Comparative Examples 2 to 4 and Example and a buffer solution were added to the respective holes and the culture medium was incubated at 37° C. for 1 hr to evaluate the antibacterial activity. Furthermore, a sterilized culture medium was stratified on the solidified culture medium and was left to stand at room temperature to be solidified, followed by static culture in an incubator at 37° C. After 20 hr, the diameter of the clear zone formed in the periphery of each hole perforated in the culture medium was measured. The results are shown in FIG. 5

The magnitude of the antibacterial activity of the electrolyzed water not containing any additive of Comparative Example 2 was the lowest and was approximately the same as that of the mouthwash containing a menthol and an organic solvent of Comparative Example 3. In contrast, it was observed that the magnitude of the antibacterial activity was slightly large in the electrolyzed water containing SDS of Comparative Example 4 and was the largest in the liquid mouthwash containing a menthol and SDS of Example of the present invention.

[Evaluation of Bactericidal Effect 2]

The effect of the liquid mouthwash of the present invention on caries-causing bacteria (*S. mutans* and *Lactobacillus*) was compared with that of a commercially available mouthwash not containing electrolyzed water. Bacteria were collected after the use of the liquid mouthwash of Example and a commercially available mouthwash (containing 0.2 g of benzethonium chloride in 100 g of the mouthwash) as Comparative Example 5 and were plate cultured on *Mitis Salivarius* agar culture medium or Difco Rogosa SL agar culture medium at 37° C. for 48 hr, followed by counting the number of colonies (CFU/mL). In addition, as a control experiment, the same procedure was performed with a buffer solution (PBS).

Figure 6:
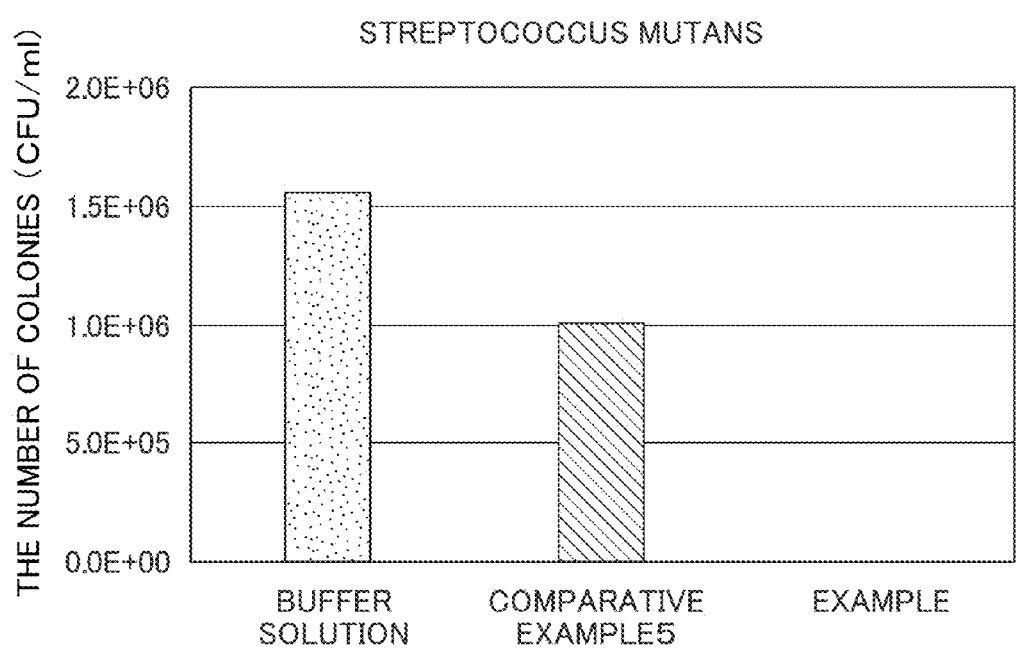
FIG. 6 is a graph showing the bactericidal activity of the liquid mouthwash of the present invention on *Streptococcus mutans* (*S. mutans*) bacteria (the main caries-causing bacteria).
Figure 7:
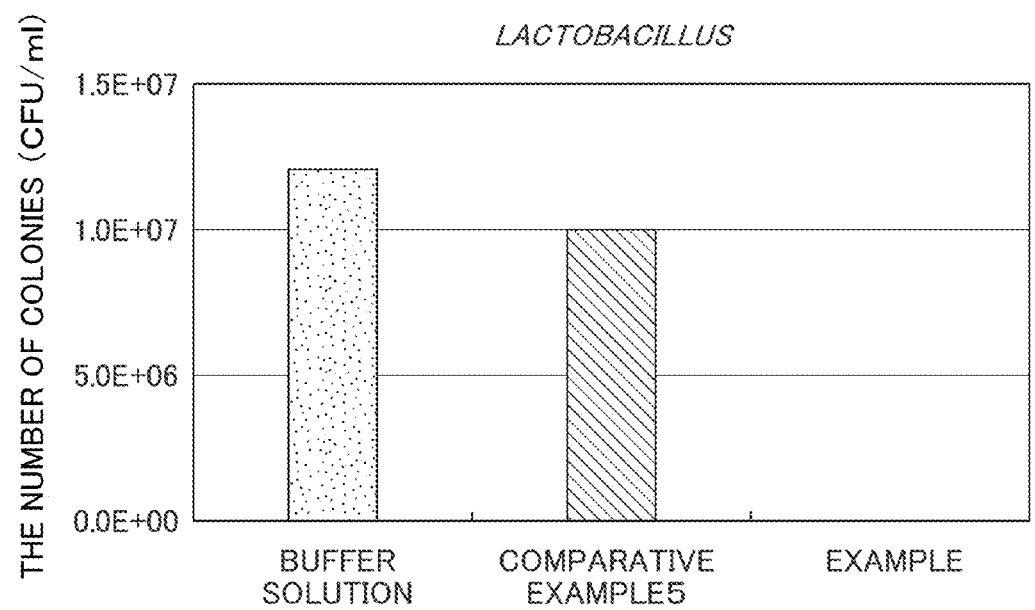
FIG. 7 is a graph showing the bactericidal activity of the liquid mouthwash of the present invention on *Lactobacillus* bacteria (chronic caries-causing bacteria).
Figure 8:
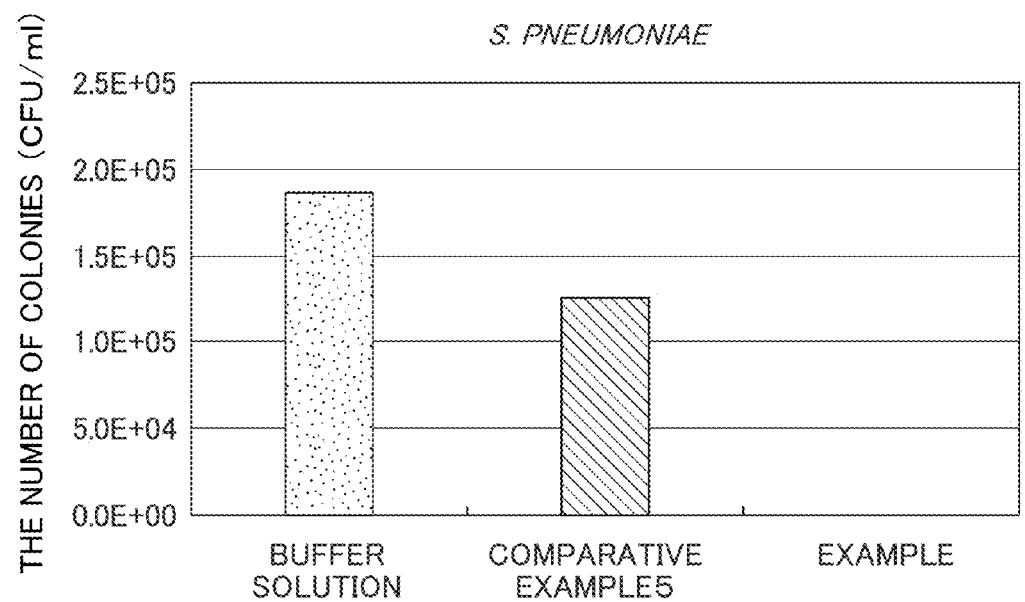
FIG. 8 is a graph showing the bactericidal activity of the liquid mouthwash of the present invention on *S. pneumoniae* (bacteria causing aspiration pneumonitis).

FIG. 6 shows the number of colonies after culturing bacteria on which the buffer solution or the mouthwash of Comparative Example 5 or Example acted. In the use of the mouthwash of Example, the bacteria were dead, and no colony was found. In contrast, in the use of the mouthwash of Comparative Example 5, the number of colonies was reduced by only 30% compared with that of the control. These results demonstrated that the liquid mouthwash of the present invention has a high bactericidal effect even in comparison with a commercial mouthwash product. The same investigation was performed against *Lactobacillus* and *S. pneumoniae* (one of bacteria present in oral cavity and leading to aspiration pneumonitis). The results were the same as those against *S. mutans*.

[Confirmation of Toxicity]

The liquid mouthwashes of the present invention, the Comparative Example 5 and Example were verified for the influence on the epithelial cells in oral cavity by gargling with the mouthwashes for 20 sec and observing the epithelial cells collected from the oral cavity. The commercially available liquid mouthwash containing electrolyzed water of Comparative Example 5 contained 125 ppm of chlorine and had a pH of 7.83. In contrast, the liquid mouthwash of the present invention contained 125 ppm of chlorine and had a pH of 7.

Figure 9:
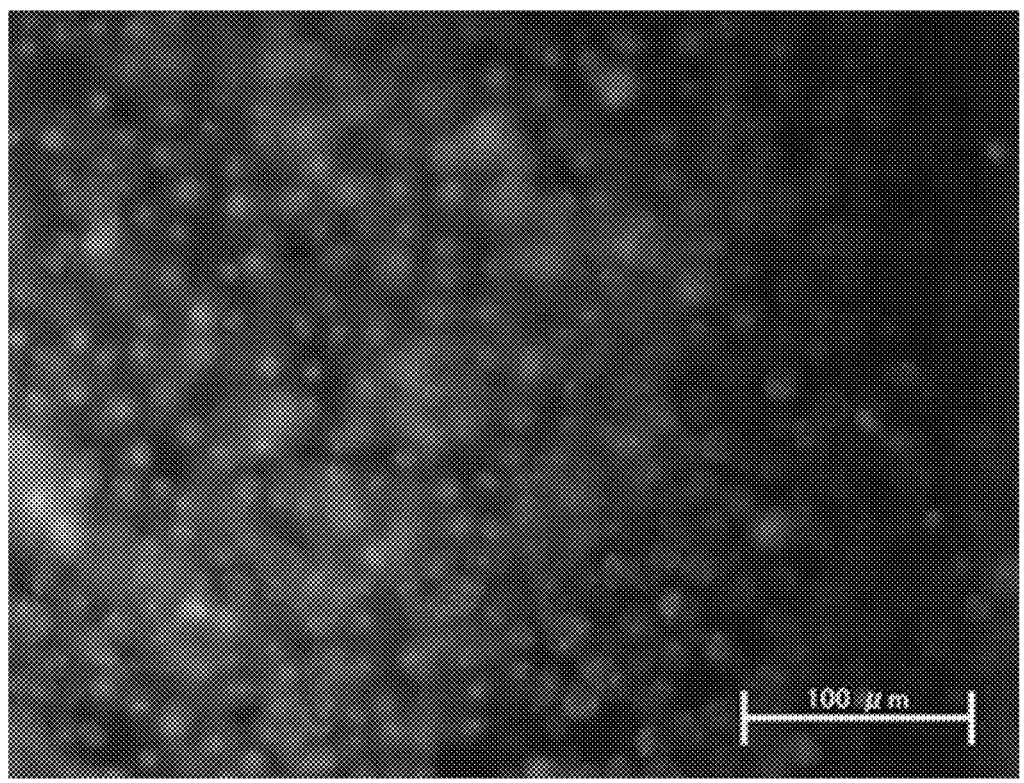
FIG. 9 is a photograph showing mucosal epithelial cells after application of a commercially available liquid mouthwash.
Figure 10:
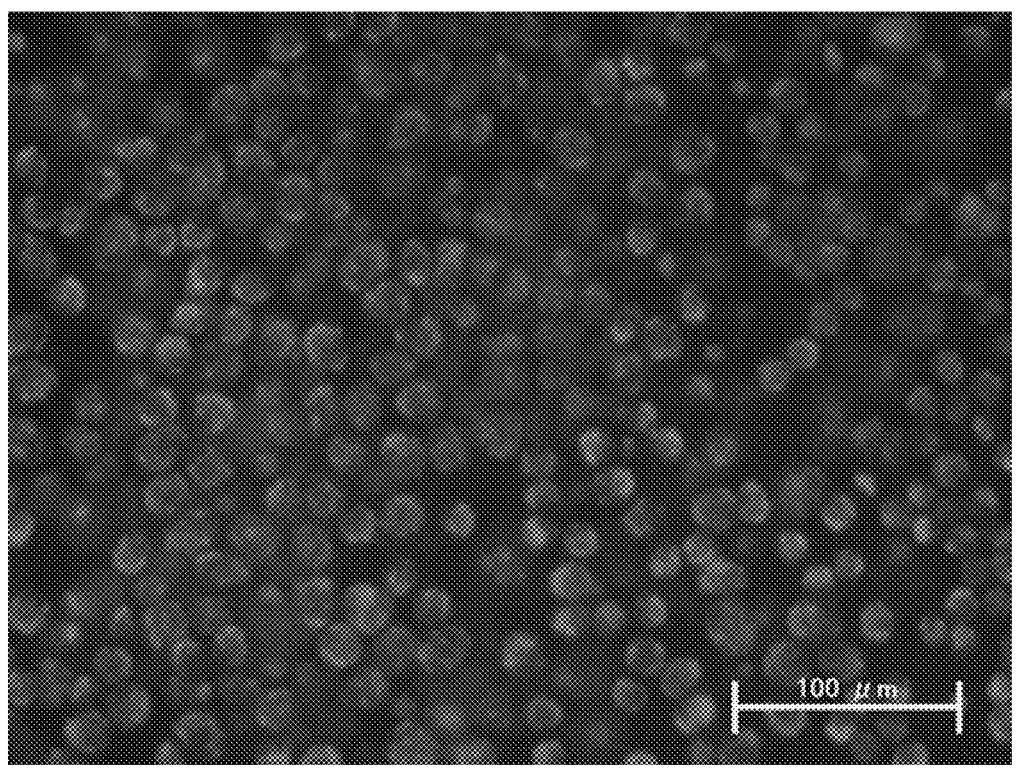
FIG. 10 is a photograph showing mucosal epithelial cells after application of the liquid mouthwash of the present invention.

FIGS. 9 and 10 show the epithelial cells immediately after the action of the mouthwashes of Comparative Example 5 and Example, respectively. In gargling with the liquid mouthwash of the present invention, almost no dead epithelial cells were found. In contrast, in the use of the liquid mouthwash of Comparative Example 5, about 30% of the epithelial cells were dead.

Figure 11:
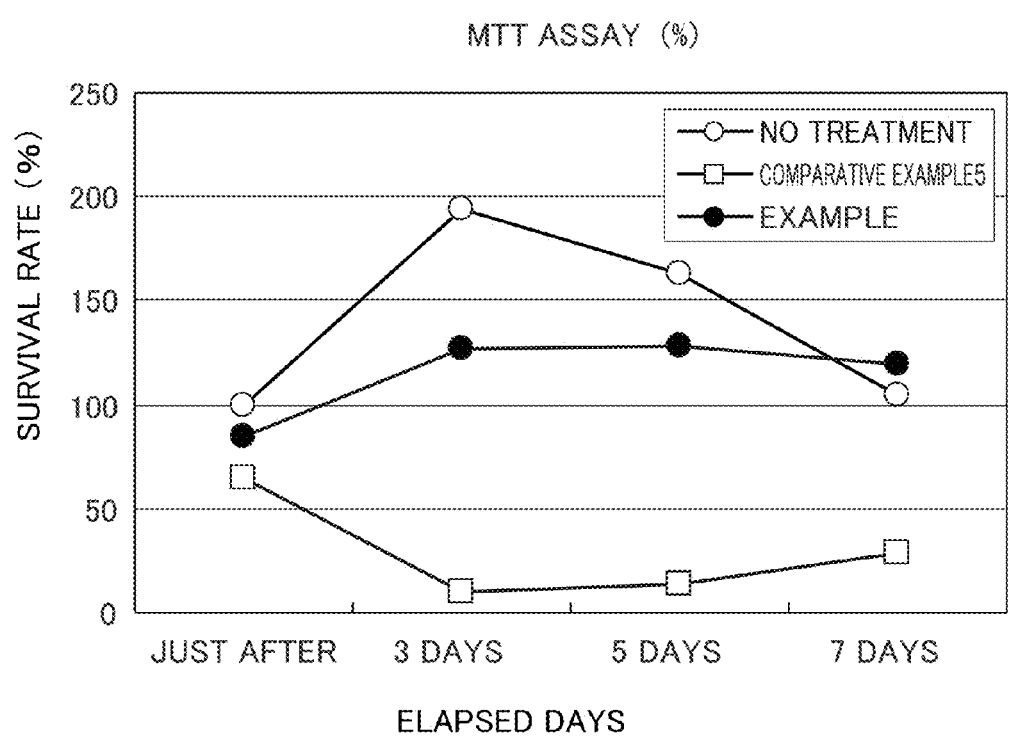
FIG. 11 is a graph showing the survival rate of mucosal epithelial cells after application of liquid mouthwashes.

Furthermore, the epithelial cells collected after gargling were cultured, and a change in the number of surviving was investigated. The number of epithelial cells immediately after the collection without treating with a mouthwash was defined as 100%. The ratio of the number of epithelial cells to this number was used for evaluation. FIG. 11 shows the survival rates of epithelial cells in no treatment, Comparative Example 1, and Example on just after, 3 days, 5 days, and 7 days after the use. In the use of the mouthwash of Comparative Example 5, almost all of the epithelial cells were dead on 3 days after the use. In contrast, in the use of the liquid mouthwash of the present invention, almost no epithelial cells were dead even after one week, and it was confirmed that the liquid mouthwash of the present invention do not substantially affect the epithelial cells in oral cavity.

The investigation above revealed that the liquid mouthwash of the present invention has a high bactericidal effect, compared with a commercially available liquid mouthwash containing electrolyzed water, while having reduced chlorine smell and less affecting oral cells.

The invention claimed is:

1. A liquid mouthwash containing electrolyzed water having a positive oxidation-reduction potential, 40 mg/L to 80 mg/L of 1-menthol, 5 mg/L to 40 mg/L of sodium dodecylsulfate, and 4.6 mol/L to 5.9 mol/L of propylene glycol, and having a pH of 7.0 to 8.

2. The liquid mouthwash according to claim 1, further containing a hydroxide of an alkali metal as an alkaline agent.

3. The liquid mouthwash according to claim 1, wherein the electrolyzed water and at least one of the menthol and the anionic surfactant are accommodated not to be in contact with each other and are mixed at the time of use.

\* \* \* \* \*